(12) United States Patent
Burns et al.

(10) Patent No.: US 8,012,414 B2
(45) Date of Patent: Sep. 6, 2011

(54) STERILIZATION OF DRUGS USING SUPERCRITICAL CARBON DIOXIDE STERILANT

(75) Inventors: David C. Burns, Ithaca, NY (US); Rebecca J. Humphrey, Liverpool, NY (US); Anthony R. Eisenhut, Lansing, NY (US); Tim W. Christensen, Greenville, NC (US)

(73) Assignee: Novasterilis, Lansing, NY (US)

( * ) Notice: Subject to any disclaimer, the term of this patent is extended or adjusted under 35 U.S.C. 154(b) by 639 days.

(21) Appl. No.: 11/889,345

(22) Filed: Aug. 10, 2007

(65) Prior Publication Data

US 2009/0041620 A1    Feb. 12, 2009

(51) Int. Cl.
*A61L 2/20* (2006.01)
*A61L 2/00* (2006.01)

(52) U.S. Cl. ............................................ 422/33; 422/28

(58) Field of Classification Search ............... 422/33, 422/28
See application file for complete search history.

(56) References Cited

U.S. PATENT DOCUMENTS

| | | | |
|---|---|---|---|
| 5,996,155 A * | 12/1999 | Chao et al. ................ | 8/158 |
| 2004/0033269 A1 * | 2/2004 | Hei et al. .................. | 424/616 |
| 2010/0080790 A1 * | 4/2010 | Matthews et al. ......... | 424/94.61 |

FOREIGN PATENT DOCUMENTS

EP        1782839 A1 *    5/2007

* cited by examiner

*Primary Examiner* — Kevin C Joyner
(74) *Attorney, Agent, or Firm* — Welsh Flaxman & Gitler LLC

(57) ABSTRACT

A sterilization method for drugs to achieve a 6-log reduction in CFUs of industry standard bacteria and bacterial spores is effective by subjecting the drugs to a chemical additive-containing carbon dioxide sterilant fluid at or near its supercritical pressure and temperature conditions and controlling the pressurization and depressurization rates.

8 Claims, 1 Drawing Sheet

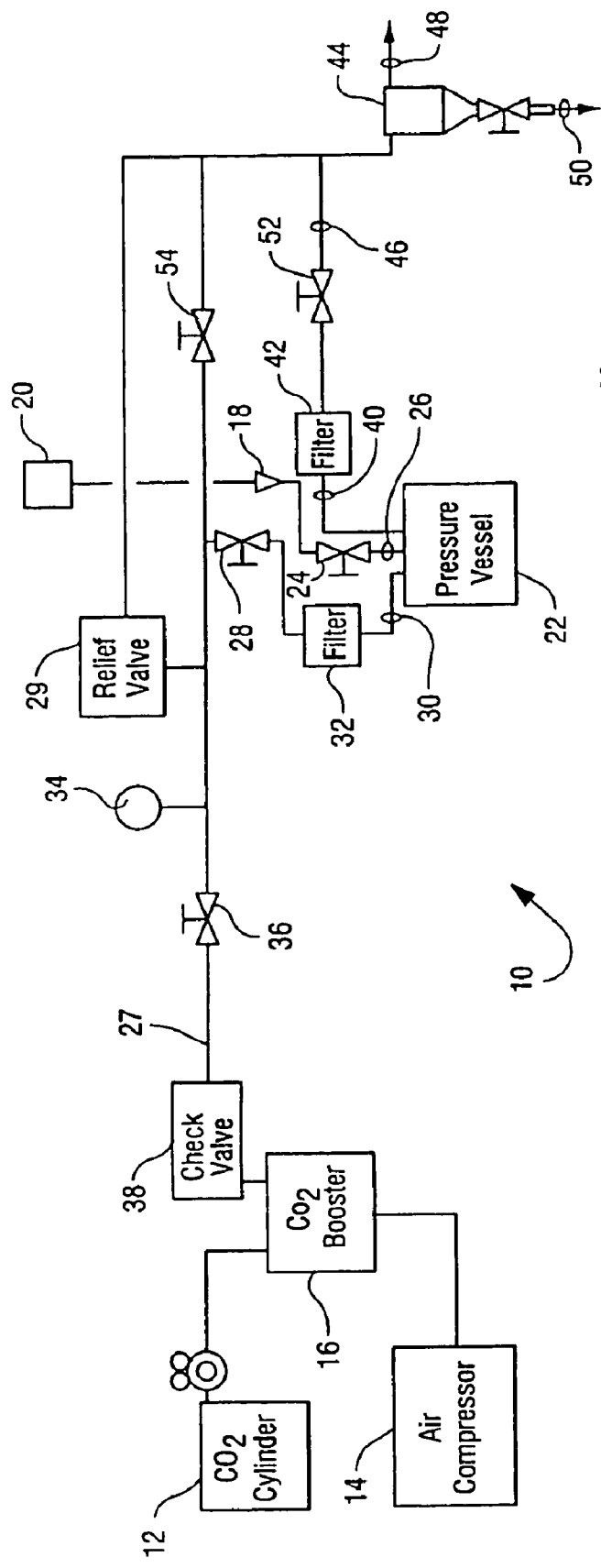
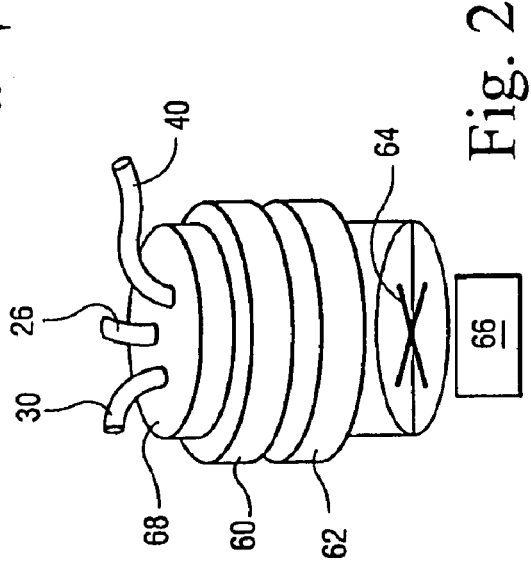
Fig. 1
Fig. 2

US 8,012,414 B2

STERILIZATION OF DRUGS USING SUPERCRITICAL CARBON DIOXIDE STERILANT

FIELD OF THE INVENTION

The present invention relates generally to sterilization a method for drugs, in particular, micro-crystalline or powder form drugs. Supercritical carbon dioxide is employed as a sterilization fluid, and the pressurization and depressurization rates ate controlled.

BACKGROUND OF THE INVENTION

A need has developed for a gentle and reliable sterilization method that results in greater than $10^6$ log reductions of microbial and viral contaminants of the material to be sterilized without impacting the properties of the material being sterilized. Many new medical advances cannot be implemented because the sterilization industry is unable to provide a suitable sterilant as part of the manufacturing process.

In the case of polymers, gamma irradiation has been shown to compromise the mechanical properties. Furthermore, steam sterilization is incompatible with thermally or hydrolytically labile polymers. Ethylene oxide (EtO), a common and widely used sterilant, is toxic, mutagenic, and a carcinogenic substance that can react with some polymers, and also requires prolonged periods of outgassing. However, the use of EtO in the sterilization of drugs has fallen out of favor and is in fact outlawed in some countries.

Biological tissues, including macromolecular biopolymers, are also incompatible with steam. Gamma radiation results in a significant decrease in tissue integrity and bone strength. Certain antibacterial washes have been used to disinfect tissue, but incomplete sterilization is achieved and the washes leave residual toxic contaminants in the tissues. Ethylene oxide also reacts with biological tissue and is thus an undesirable sterilant for such reason.

Many medical devices, such as stents, catheters and endoscopes, are fabricated from, or coated with, sensitive polymers that cannot tolerate steam, irradiation, or ethylene oxide. Plasma sterilization has been shown to be incompatible with some medical equipment and leaves toxic residues.

Recently, in U.S. Pat. No. 6,149,864 to Dillow et al (the entire content of which is expressly incorporated hereinto by reference), the use of supercritical $CO_2$ was disclosed as an alternative to existing technologies for sterilizing a wide range of products for the healthcare industry with little or no adverse effects on the material treated. Specifically, the Dillow '864 patent disclosed the inactivation of a wide range of vegetative microbial cells using supercritical carbon dioxide with agitation and pressure cycling. However, only one spore-forming bacterium was investigated in the Dillow '864 patent, specifically, B. cereus. No disclosure appears in Dillow '864 patent regarding the efficacy of the therein suggested techniques using currently accepted bio-indicator standards used to judge sterilization (i.e., B. stearothermophilus and B. subtilis). Subsequently, however, other investigators achieved only a 3.5 log reduction in B. subtilis spores using the method disclosed in the Dillow et al '864 patent.

Even more recently, in U.S. Pat. No. 7,108,832 to Christensen et al. (the entire content of which is expressly incorporated hereinto by reference), the use of supercritical $CO_2$ was disclosed as an alternative to existing technologies for sterilizing a wide range of products for the healthcare industry with little or no adverse effects on the material treated.

Bacterial spores are more difficult to sterilize than vegetative cells. B. steamthermophilus and B. subtilis spores represent the greatest challenge to sterilization methods (FDA 1993) and are the currently accepted standards within the industry for validating sterilization methods. Sterilization is defined as greater than or equal to a 6-log ($10^6$) reduction in colony forming units (CFUs). Reproducible inactivation of these resistant microbes is required for commercialization of novel sterilization equipment and processes.

It, therefore, would be highly desirable if a sterilization method for drugs could be provided which is effective to achieve a 6-log reduction in CFUs of industry standard bacterial spores. It would more specifically be especially desirable if a sterilization method for micro-crystalline and powder form drugs could be provided that achieves a 6-log reduction in CFUs and retains the original micro-crystalline and/or powder form state of the drug. The present invention is therefore directed to fulfilling such needs.

SUMMARY OF THE INVENTION

Broadly, a sterilization method is provided by the present invention which is effective in achieving a 6-log reduction in CFUs of industry standard bacterial spores when treating micro-crystalline and powder form drugs. More specifically, a sterilization method is provided which is effective to achieve a 6-log reduction in CFUs of B. stearothermophilus and B. subtilis spores. These 6-log reductions are achieved by the present invention by subjecting sterilizable materials under controlled sterilization pressure and temperature conditions using a chemical additive-containing supercritical carbon dioxide as a sterilant fluid. Most preferably, the chemical additive-containing supercritical carbon dioxide sterilant fluid is agitated during sterilization.

It is further an object of the present invention to provide a drug sterilization method comprising (a) placing a drug in a micro-crystalline or powder form state in need of sterilization in a vessel with a sterilization enhancing effective amount of a chemical sterilization additive, (b) regulating the pressurization rate of the vessel to bring the drug into contact with a sterilant fluid comprised of carbon dioxide at or near its supercritical pressure and temperature conditions, (c) maintaining the contact with the sterilant fluid under the temperature and pressure conditions for a time sufficient to achieve a 6-log reduction or greater in colony forming units (CFUs), and then (d) regulating the depressurization rate of the vessel until ambient operating conditions are reached, whereby by regulating the pressurization and depressurization rates the state of the drug remains unchanged.

It is also an object of the present invention to provide a drug sterilization method including the step of agitating the sterilant fluid while the vessel is pressurized.

It is also another object of the present invention to provide a drug sterilization method wherein the step of agitating the sterilant fluid is practiced by subjecting the sterilant fluid to the mechanical agitation of stirring.

It is also a further object of the present invention to provide a drug sterilization method wherein the chemical sterilization additive is selected from the group consisting of hydrogen peroxide, acetic acid, peracetic acid and trifluoroacetic acid and/or a mixture thereof.

It is still another object of the present invention to provide a drug sterilization method wherein the drug is a steroid or other similar drugs in a micro-crystalline or powder form state.

It is yet another object of the present invention to provide a drug sterilization method wherein the step of regulating the pressurization rate of the vessel occurs at 0.1-5 psi per second until operating conditions are reached and the step of regulating the depressurization rate of the vessel until ambient operating conditions are reached occurs at less than 75 psi per second.

It is a further object of the present invention to provide a drug sterilization method wherein the sterilization additive is present in an amount of between about 0.001% to about 2.0% based on the total volume of the sterilant fluid.

It is still a further object of the present invention to provide a drug sterilization method wherein pressurization occurs at a rate of 0.1-5 psi per second until 1500 psi is reached.

It is also an object of the present invention to provide a drug sterilization method wherein the pressure is maintained at 1500 psi for 60 to 180 minutes and then regulated depressurization occurs.

It is also another object of the present invention to provide a drug sterilization method wherein depressurization occurs at a rate of 0.1-75 psi per second until ambient conditions are reached.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein;

FIG. 1 is a schematic view of a presently preferred sterilization apparatus in accordance with the present invention; and FIG. 2 is a detailed schematic view of the pressure vessel employed in the apparatus of FIG. 1.

DETAILED DESCRIPTION OF THE INVENTION

The sterilization apparatus and methods of the present invention are usefully employed to sterilize a variety of materials, biological tissues, instruments, and devices that are thermally or hydrolytically unstable, or otherwise incompatible with conventional sterilization techniques, or where such techniques are not preferred. Examples of materials that may be sterilized by the present invention include, but are not limited to, biodegradable polymers such as poly(lactic acid) (PLA) or poly(lactic-co-glycolic acid) (PLGA)-based polymers, which can be used in various embodiments as implantable drug delivery devices; tissues for implantation or transplantation, including but not limited to, bone, cartilage, ligament, or other connective or musculoskeletal tissue for allografts in the treatment of orthopaedic trauma and joint reconstruction; grafted or artificial skin tissue for the treatment of burns and other dermal abrasions or damage; medical devices, such as cardiac or urological stents and catheters, including drug- or gene-coated stents and catheters, rigid and flexible endoscopes for orthopaedic, plastic, and gastroenterological surgery; drug delivery devices, including, but not limited to, implantable polymer devices, polymer microspheres, or other specifically shaped drug-releasing devices comprised of PLA, PLGA, or other biodegradable polymers, and drugs in solid including but not limited to micro-crystalline and powder forms or liquid forms (i.e., any substance or active agent used in the diagnosis, treatment or prevention of a disease or illness).

As noted previously, 6-log reductions in CFUs may be achieved in accordance with the present invention by subjecting materials to be sterilized under sterilization temperature and pressure conditions using a chemical additive-containing supercritical carbon dioxide as a sterilant fluid, and especially where the sterilant fluid is agitated during the sterilization process.

Most preferably, the sterilant is carbon dioxide at or near its supercritical pressures and temperature conditions. Thus, the sterilization process of the present invention is practiced using carbon dioxide as a sterilant at pressures between about 1000 psi to about 3500 psi, at temperatures in the range between about 25° C. to about 60° C. Most preferably, the article to be sterilized is subject to carbon dioxide at or near such pressure and temperature conditions for times ranging from about 20 minutes to about 12 hours. The carbon dioxide employed in the practice of the present invention is most preferably substantially pure. Thus, trace amounts of other gases may be tolerated provided that the sterilization properties of the carbon dioxide are not impaired. For ease of further discussion below, the term "supercritical carbon dioxide" will be used, but it will be understood that such a term is non-limiting in that carbon dioxide within the pressure and temperature ranges as noted immediately above may be employed satisfactorily in the practice of the present invention.

The chemical additives employed in the present invention most preferably include peroxides and/or carboxylic acids. Preferred carboxylic acids include alkanecarboxylic acids and/or alkanepercarboxylic acids, each of which may optionally be substituted at the alpha carbon with one or more electron-withdrawing substituents, such as halogen, oxygen and nitrogen groups. Particularly preferred species of chemical additives employed in the practice of the present invention include hydrogen peroxide ($H_2O_2$), acetic acid (AcA), peracetic acid (PAA) and trifluoroacetic acid (TFA), and mixtures thereof One particularly preferred liquid additive that may be employed in the practice of the present invention is commercially available Sporeclenz® sterilant, which is a mixture of acetic acid with hydrogen peroxide and peracetic acid.

The chemical sterilization additive is employed in a sterilization enhancing effective amount of at least about 0.001 vol. % and greater, based on the total volume of the carbon dioxide. The amount of sterilization additive will be dependent upon the particular sterilization additive that is employed. Thus, for example, peracetic acid may be present in relatively small amounts of about 0.005 vol. % and greater, while acetic acid may need to be employed in amount of about 1.0 vol. % and greater. Thus, a range of at least about 0.001 vol. % and greater, up to about 2.0 vol. % will typically be needed in order to achieve a sterilization enhancing effect in combination with carbon dioxide.

One presently preferred embodiment of an apparatus 10 according to the present invention is depicted in accompanying FIGS. 1 and 2. In this regard, it can be seen that the apparatus includes a standard compressed gas cylinder 12 containing carbon dioxide, and a standard air compressor 14 used in operative association with a carbon dioxide booster 16 (e.g., Haskel Booster AGT 7/30). Alternatively, the air compressor 14 and carbon dioxide booster 16 can be replaced with a single carbon dioxide compressor.

An additive cycle is also provided by means of an inlet port 18 which allows additive contained in reservoir 20 to be added to a reactor pressure vessel 22 through valve 24 and additive line 26. Alternatively, the additive can be introduced by soaking it into an absorbent pad and placing the pad in the reactor pressure vessel 22 with the material to be treated. The carbon dioxide is introduced to the reactor pressure vessel 22 from header line 27 via valve and regulator (herein called valve 28) and $CO_2$ supply line 30. A filter 32 (e.g., a 0.5 micron filter) is provided in the supply line 30 to prevent the escape of material from the vessel. A pressure gauge 34 is provided downstream of $CO_2$ shut-off valve 36 in supply header line 27 to allow the pressure to be visually monitored. A check valve 38 is provided in the header line 27 upstream of the $CO_2$ shut-off valve 36 to prevent reverse fluid flow into the carbon dioxide booster 16. In order to prevent an overpressure condition existing in header line 27, a pressure relief valve 9 may be provided.

An outlet line 40 through valve and regulator (herein called valve 52) allows the reactor pressure vessel 22 to be depressurized. In this regard, the depressurized fluid exits the reactor pressure vessel 22 via outline line 40, is filtered by filter unit 42 and then is directed to separator 44 where filtered $CO_2$ gas may be exhausted via line 48, and liquid additive collected via line 50 for possible reuse. Valves 52, 54 may be provided in lines 46 and 27, respectively, to allow fluid isolation of upstream components.

The reactor pressure vessel 22 is most preferably constructed of stainless steel (e.g., 316 gauge stainless steel) and has a total internal volume sufficient to accommodate the materials being sterilized either on a laboratory or commercial scale. For example, in laboratory studies, an internal volume of 600 mL (e.g., approximately 8 inches long by about 2.5 inches inside diameter) was deemed adequate As is perhaps more clearly shown in FIG. 2, the reactor pressure vessel 22 includes a vibrator 60, a temperature control unit 62, and a mechanical stirring system most preferably comprised of an stirring impeller 64 and a magnetic driver 66. The reactor pressure vessel 22 contains a conventional basket (not shown) which is also preferably constructed of 316 gauge stainless steel. The basket serves to hold the items to be sterilized as well as to protect the stirring impeller 64 and direct the sterilant fluid in a predetermined manner.

The reactor pressure vessel 22 may be operated at a constant pressure or under continual pressurization and depressurization (pressure cycling) conditions without material losses due to splashing or turbulence, and without contamination of pressure lines via back diffusion. The valves 24, 28 and 52 allow the reactor pressure vessel 22 to be isolated and removed easily from the other components of the apparatus 10. The top 68 of the reactor pressure vessel 22 may be removed when depressurized to allow access to the vessel's interior.

In use, the material to be sterilized is introduced into the interior space of the reactor pressure vessel 22 along with any initial portion of liquid sterilization additive from reservoir 20 or an additive pad. The temperature control unit 62 is operated so as to set the desired initial temperature for sterilization. The reactor pressure vessel 22 may then be pre-equilibrated with carbon dioxide from gas cylinder 12 at atmospheric pressure, following which the magnetic driver 66 is operated so as to activate the stirring impeller 64. The reactor pressure vessel 22 may thereafter be pressurized to a desired pressure by introducing additional carbon dioxide gas from gas cylinder 12 via the air compressor 14 linked to carbon dioxide booster 16.

In order to affect a pressure cycling of the reactor pressure vessel 22, an amount of carbon dioxide may be released therefrom via depressurization outline line 40 by momentarily opening valve 52 sufficient to partially reduce pressure within the reactor pressure vessel 22. Additive may be introduced into the reactor pressure vessel 22 for any given pressure cycle by opening valve 24 which allows liquid additive to flow from reservoir 20 into inlet port 18. It will be understood that the sterilization additives may be introduced prior to pressurization and/or during pressure cycling. Prior to pressurization, additives are introduced directly into the reactor pressure vessel 22 prior to sealing and/or via the additive port 18. The sterilization additives are most preferably introduced during the cycling stages by measured addition to the additive port 18 at ambient pressures. The port 18 is subsequently sealed and the additive chamber is pressurized so that the additive may enter the reactor pressure vessel 22 without altering the internal pressure. The exact mechanism of addition may be modified such that the process is more efficient and/or convenient.

Following additive introduction, the reactor pressure vessel 22 may be repressurized to a desired pressure following introduction of the liquid additive therein. Such depressurization/repressurization with introduction of liquid additive may be repeated for any number of cycles that may be desired. The cycle of depressurization and repressurization as well as the introduction of the carbon dioxide and liquid additive may be automatically controlled via a controller screen which sequences the various valves discussed previously so as to achieve the desired pressure conditions and cycles.

In the treatment of micro-crystalline and powder form drugs it has been found that if you do not precisely control the pressurization and depressurization rates in the sterilization vessel the drugs become unusable. For these products, the input or flow of $CO_2$ through valve 24 into the reactor pressure vessel 22 is regulated to 0.01 to 5 psi/second. Regulating the rate of pressurization is also intended to control mass flow (1000 mg/second) of $CO_2$ into the reactor pressure vessel 22. In the initial fill, the valve 24 is opened and allowed to flow at the regulated rate using the ambient pressure of the $CO_2$ supply from the gas cylinder 12. The $CO_2$ supply pressure can range from 75 psi to approximately 900 psi or greater. Once the pressure in reactor pressure vessel 22 reaches equilibrium with the $CO_2$ supply source pressure, the pumping of the $CO_2$ using the carbon dioxide booster 16 begins. The $CO_2$ booster rate of pressurization is regulated to not exceed 5 psi/second. Once the reactor pressure vessel 22 reaches its operating pressure of 1500 psi, the process is allowed to continue through its normal path. Upon completion of the desired time period at the operating temperature and pressure, depressurization of the reactor pressure vessel 22 then occurs. At this point the output valve 52 is opened enough that the rate of depressurization is regulated to 75 psi/second or less. Regulating the rate of depressurization is also intended to control of mass flow of $CO_2$ out of the reactor pressure vessel 22. The rate of depressurization is controlled at this rate until the ambient pressure in the reactor pressure vessel 22 is zero or at equilibrium with the atmospheric pressure. Ambient conditions are generally zero psi and 25 degrees C.

Most preferably, periodic agitation to the contents of reactor pressure vessel 22 is effected using a vibrator 60 through the entire process. Intermittent or continuous agitation of the reactor pressure vessel 22 and its contents is performed by vibrating the reactor pressure vessel 22 during sterilization. Agitation enhances mass transfer of the carbon dioxide and additives by eliminating voids in the fluid such that the material being sterilized comes into more complete contact with sterilant. The specific means of agitation may be adjusted to accommodate the particular apparatus employed and to optimize sterilization times, temperatures, and pressure cycles. When sterilization is complete, the reactor pressure vessel 22 is depressurized, the magnetic driver 66 is stopped thereby stopping the stirring impeller 64, and the thus sterilized material removed by opening top 68 of reactor pressure vessel 22.

The present invention will be further understood after careful consideration is given to the following Examples.

EXAMPLE 1

Effective Sterilization

The apparatus generally depicted in FIGS. 1 and 2 was employed for this Example. A sample of Methyl-Prednisone, a Corticosteroid was placed in a gas permeable bag or pouch made from a material such as Tyvek. The Corticosteroid was observed to be a fine powder-like substance that was dry to the touch. The pouch or bag was then sealed. The pouch was then placed in a stainless steel basket. An additive, Peracetic Acid (16 mL), was transferred by syringe onto the surface of a cotton pad and placed in the basket. The basket was then loaded into the 20 L reactor pressure vessel 22. The reactor pressure vessel 22 was regulated to pressurize with $CO_2$ at a rate of 5 psi/second as discussed above and heated to 35° C. Stirring and agitation mechanisms were activated and the reactor vessel eventually reached 1500 psi. The process continued for 180 minutes, that is stirring while maintaining the vessel at 1500 psi and a temperature of 35° C. After 180 minutes the depressurization step began. During depressurization the $CO_2$ pressure was then regulated to drop to 0 psi at a rate of 50 psi/second. The pouch with the Corticosteroid was removed from the vessel and the drug was examined. The state of the Corticosteroid drug was observed to be unchanged, however, it was now sterilized. The drug continued to look and feel like a fine powder that was dry to the touch.

EXAMPLE 2

Non-Effective Sterilization

The apparatus generally depicted in FIGS. 1 and 2 was employed for this Example. A sample of Methyl-Prednisone, a Corticosteroid was placed in a gas permeable bag or pouch made from a material such as Tyvek. The Corticosteroid was observed to be a fine powder-like substance that was dry to the touch. The pouch or bag was then sealed. The pouch was then placed in a stainless steel basket. An additive, Peracetic Acid (16 mL), was transferred by syringe onto the surface of a cotton pad and placed in the basket. The basket was then loaded into the 20 L reactor pressure vessel 22. The reactor pressure vessel 22 was regulated to pressurize with $CO_2$ at a rate of 75 psi/second and heated to 35° C. The pressurization rate was achieved by opening the valve from the $CO_2$ and was allowed to pressurize unrestricted from the ambient pressure of the $CO_2$ supply. Stirring and agitation mechanisms were activated and the reactor vessel eventually reached 1500 psi. The process continued for 180 minutes, that is stirring while maintaining the vessel at 1500 psi and a temperature of 35° C. After 180 minutes the depressurization step began. During depressurization the $CO_2$ pressure was then allowed to drop to 0 psi at a rate of 100 psi/second. The pouch with the Corticosteroid was removed from the vessel and the drug was examined. The state of the Corticosteroid drug was observed to have changed. The drug looked clumped and felt clumped. The drug was inconsistent in particle size. The clump size ranged from solid pieces from 2 inches to ½ inch with various pieces intermixed. Thus complete sterilization could not be confirmed and the drug was unusable.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the present invention.

What is claimed is:

1. A drug sterilization method comprising (a) placing a drug in a micro-crystalline or powder form state in need of sterilization in a vessel with a sterilization enhancing effective amount of a chemical sterilization additive, (b) regulating a pressurization rate of the vessel to bring the drug into contact with a sterilant fluid comprised of carbon dioxide at or near the supercritical pressure and temperature conditions of said carbon dioxide, (c) maintaining said contact with the sterilant fluid under said temperature and pressure conditions for a time sufficient to achieve a 6-log reduction or greater in colony forming units (CFUs), and then (d) regulating a depressurization rate of the vessel such that depressurization occurs at a rate of 0.1-75 psi per second until ambient operating conditions are reached, whereby by regulating the pressurization and depressurizations rates, the state of the drug remains unchanged.

2. The drug sterilization method of claim 1, which further comprises agitating the sterilant fluid while the vessel is pressurized.

3. The drug sterilization method of claim 2, wherein said step of agitating the sterilant fluid is practiced by subjecting the sterilant fluid to mechanical agitation of stirring.

4. The drug sterilization method of claim 1, wherein the chemical sterilization additive is selected from the group consisting of hydrogen peroxide, acetic acid, peracetic acid and trifluoroacetic acid and/or a mixture thereof.

5. The drug sterilization method of claim 1, wherein the drug is a steroid or other similar drugs in a micro-crystalline or powder form state.

6. The drug sterilization method of claim 1, wherein the sterilization additive is present in an amount of between about 0.001% to about 2.0% based on the total volume of the sterilant fluid.

7. The drug sterilization method of claim 1, wherein pressurization occurs at a rate of 0.1-5 psi per second until 1500 psi is reached.

8. The drug sterilization method of claim 1, wherein the pressure is maintained at 1500 psi for 60 to 180 minutes and then regulated depressurization occurs.

* * * * *